United States Patent
Nakai et al.

(10) Patent No.: US 10,660,611 B2
(45) Date of Patent: May 26, 2020

(54) COMPOSITION FOR ACOUSTIC WAVE PROBE, SILICONE RESIN FOR ACOUSTIC WAVE PROBE USING THE SAME, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

(71) Applicant: FUJIFILM Corporation, Tokyo (JP)

(72) Inventors: Yoshihiro Nakai, Kanagawa (JP); Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 14 days.

(21) Appl. No.: 16/045,938

(22) Filed: Jul. 26, 2018

(65) Prior Publication Data
US 2018/0344287 A1    Dec. 6, 2018

Related U.S. Application Data

(63) Continuation of application No. PCT/JP2017/002078, filed on Jan. 23, 2017.

(30) Foreign Application Priority Data

Jan. 28, 2016    (JP) ................. 2016-014141

(51) Int. Cl.
*C08K 3/36* (2006.01)
*A61B 8/00* (2006.01)
(Continued)

(52) U.S. Cl.
CPC .......... *A61B 8/4444* (2013.01); *A61B 5/0095* (2013.01); *A61B 8/00* (2013.01);
(Continued)

(58) Field of Classification Search
None
See application file for complete search history.

(56) References Cited

U.S. PATENT DOCUMENTS 4,025,485 A * 5/1977 Kodama ................. C08L 83/04
                                                           524/729
4,340,090 A    7/1982 Matsushita et al.
(Continued)

FOREIGN PATENT DOCUMENTS

EP    2 679 636 A1    1/2014
JP    2002-095081 A   3/2002
(Continued)

OTHER PUBLICATIONS

Kopylov et al. "Silica fillers for silicone rubber" Kauchuk i Rezina, 2010, 5, 32-43. (Year: 2010).*

(Continued)

*Primary Examiner* — Robert S Loewe
(74) *Attorney, Agent, or Firm* — Sughrue Mion, PLLC

(57) ABSTRACT

Provided is a composition for an acoustic wave probe including a polysiloxane mixture containing polysiloxane having a vinyl group, polysiloxane having two or more Si—H groups in a molecular chain, and silica particles of which an average primary particle diameter exceeds 16 nm and less than 100 nm and which are subjected to surface treatment, a silicone resin for an acoustic wave probe, the acoustic wave probe, an acoustic wave measurement apparatus, an ultrasound diagnostic apparatus, an ultrasound probe, a photoacoustic wave measurement apparatus, and an ultrasound endoscope.

17 Claims, 1 Drawing Sheet

(51) Int. Cl.
  *A61B 8/12* (2006.01)
  *C08K 13/06* (2006.01)
  *C08K 9/06* (2006.01)
  *A61B 8/13* (2006.01)
  *H04R 17/00* (2006.01)
  *A61B 5/00* (2006.01)
  *C08L 83/04* (2006.01)
  *G01S 7/521* (2006.01)
  *G10K 11/30* (2006.01)

(52) U.S. Cl.
  CPC .............. *A61B 8/12* (2013.01); *A61B 8/13* (2013.01); *A61B 8/4488* (2013.01); *C08K 3/36* (2013.01); *C08K 9/06* (2013.01); *C08K 13/06* (2013.01); *C08L 83/04* (2013.01); *G01S 7/521* (2013.01); *G10K 11/30* (2013.01); *H04R 17/00* (2013.01); *C08L 2203/02* (2013.01); *C08L 2205/025* (2013.01)

(56) References Cited

U.S. PATENT DOCUMENTS

| | | | | |
|---|---|---|---|---|
| 4,442,060 A * | 4/1984 | Bouverot | ................ | C08K 3/36 264/328.2 |
| 4,651,850 A * | 3/1987 | Matsuo | ................ | G10K 11/30 181/175 |
| 4,842,837 A * | 6/1989 | Shimizu | ................ | B82Y 30/00 423/335 |
| 4,985,477 A * | 1/1991 | Collins | ................ | C08K 9/06 106/490 |
| 5,013,772 A | 5/1991 | Fujiki et al. | | |
| 5,028,653 A * | 7/1991 | Desmonceau | ....... | A61K 9/1641 523/209 |
| 5,268,396 A * | 12/1993 | Lai | ................ | C08F 30/08 522/28 |
| 5,691,401 A * | 11/1997 | Morita | ................ | C08J 3/128 523/435 |
| 5,700,853 A * | 12/1997 | Yoshida | ................ | C08K 3/36 523/204 |
| 5,834,110 A * | 11/1998 | Misawa | ................ | H01B 17/325 428/328 |
| 5,977,243 A * | 11/1999 | Barthel | ................ | C08G 77/045 524/588 |
| 6,011,105 A * | 1/2000 | Ota | ................ | C08K 3/36 524/494 |
| 6,294,635 B1 * | 9/2001 | Achenbach | .......... | C08K 5/0091 528/15 |
| 7,332,144 B2 * | 2/2008 | Konya | ................ | B82Y 30/00 106/287.13 |
| 7,563,839 B2 * | 7/2009 | Scholz | ................ | C08K 3/36 523/212 |
| 7,972,431 B2 * | 7/2011 | Meyer | ................ | C09C 1/3081 106/482 |
| 8,071,693 B2 * | 12/2011 | Banerjee | ............ | C08G 73/106 525/431 |
| 9,012,586 B2 * | 4/2015 | Yoshitake | ............ | H01L 33/56 428/447 |
| 2005/0070801 A1 * | 3/2005 | Yamashita | ........... | A61B 8/4281 600/459 |
| 2007/0191537 A1 * | 8/2007 | Meyer | ............ | B82Y 30/00 524/588 |
| 2007/0282204 A1 * | 12/2007 | Yamashita | ............ | G10K 11/02 600/459 |
| 2008/0303381 A1 * | 12/2008 | Yuuya | ............ | C08K 3/22 310/327 |
| 2008/0312537 A1 * | 12/2008 | Hyuga | ............ | B06B 1/0622 600/459 |
| 2009/0243436 A1 | 10/2009 | Rubinsztajn et al. | | |
| 2011/0257532 A1 * | 10/2011 | Sasaki | ............ | B06B 1/00 600/459 |
| 2012/0123054 A1 * | 5/2012 | Matsumoto | ............ | C08K 3/22 524/701 |
| 2013/0189887 A1 * | 7/2013 | Akechi | ............ | D03D 1/02 442/60 |
| 2013/0331821 A1 * | 12/2013 | Okada | ............ | C08L 83/04 604/525 |
| 2015/0259532 A1 * | 9/2015 | Hayashida | ............ | C08K 3/36 524/493 |
| 2015/0380636 A1 * | 12/2015 | Fujisawa | ............ | C08K 3/22 524/783 |
| 2016/0122611 A1 * | 5/2016 | Yoshida | ............ | C08L 83/04 252/75 |
| 2017/0000455 A1 | 1/2017 | Nakai | | |
| 2017/0267904 A1 * | 9/2017 | Nakayama | ............ | C08K 3/00 |

FOREIGN PATENT DOCUMENTS

| | | |
|---|---|---|
| JP | 2005-125071 A | 5/2005 |
| JP | 2009-240782 A | 10/2009 |
| JP | 2015-189818 A | 11/2015 |
| WO | 2015/146308 A1 | 10/2015 |

OTHER PUBLICATIONS

Notification of Reasons for Refusal dated Apr. 9, 2019 from the Japanese Patent Office in application No. 2017-564231.
Communication dated Dec. 17, 2018 by the European Patent Office in application No. 17744120.1.
International Search Report of PCT/JP2017/002078 dated Apr. 11, 2017 [PCT/ISA/210].
Written Opinion dated Apr. 11, 2017, issued by the International Searching Authority in application No. PCT/JP2017/002078.
International Preliminary Report on Patentability dated May 7, 2018, issued by the International Searching Authority in application No. PCT/JP2017/002078.

* cited by examiner

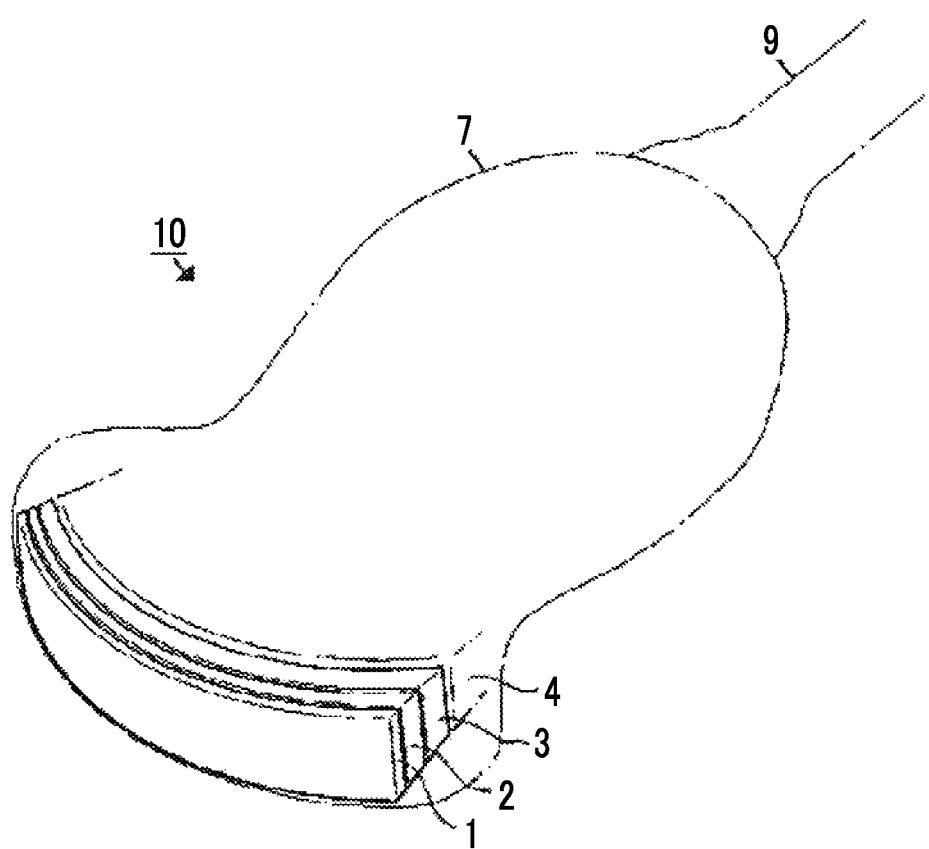

COMPOSITION FOR ACOUSTIC WAVE PROBE, SILICONE RESIN FOR ACOUSTIC WAVE PROBE USING THE SAME, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

CROSS-REFERENCE TO RELATED APPLICATIONS

This application is a Continuation of PCT International Application No. PCT/JP2017/002078 filed on Jan. 23, 2017, which claims priority under 35 U.S.C. § 119 (a) to Japanese Patent Application No. 2016-014141 filed in Japan on Jan. 28, 2016. Each of the above applications is hereby expressly incorporated by reference, in its entirety, into the present application.

BACKGROUND OF THE INVENTION

1. Field of the Invention

The present invention relates to a composition for an acoustic wave probe, a silicone resin for an acoustic wave probe using the same, the acoustic wave probe, and an ultrasound probe. Furthermore, the present invention relates to an acoustic wave measurement apparatus, an ultrasound diagnostic apparatus, a photoacoustic wave measurement apparatus, and an ultrasound endoscope.

2. Description of the Related Art

In the acoustic wave measurement apparatus, an acoustic wave probe is used which irradiates a test object or a site (hereinafter, simply referred to as an object) with an acoustic wave, receives a reflected wave (echo) thereof, and outputs a signal. An electrical signal converted from the reflected wave which has been received by this acoustic wave probe is displayed as an image. Accordingly, the interior of the test object is visualized and observed.

Acoustic waves, such as ultrasonic waves and photoacoustic waves, which have an appropriate frequency in accordance with a test object and/or measurement conditions, are selected as the acoustic waves.

For example, the ultrasound diagnostic apparatus transmits an ultrasonic wave to the interior of a test object, receives the ultrasonic wave reflected by the tissues inside the test object, and displays the received ultrasonic wave as an image. The photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave and generates heat in a case where the test object is irradiated with an electromagnetic wave pulse of visible light, near infrared light, microwave, or the like.

The acoustic wave measurement apparatus performs transmission and reception of an acoustic wave on a living body (typically, the human body) which is a test object. Therefore, it is necessary to fulfill requirements such as consistency in the acoustic impedance within the living body and/or decrease in acoustic attenuation.

For example, a probe for an ultrasound diagnostic apparatus (also referred to as an ultrasound probe) which is a kind of acoustic wave probe includes a piezoelectric element which transmits and receives an ultrasonic wave and an acoustic lens which is a portion coming into contact with a living body. An ultrasonic wave generated from the piezoelectric element is incident on the living body after being transmitted through the acoustic lens. In a case where the difference between acoustic impedance (density×acoustic velocity) of the acoustic lens and acoustic impedance of the living body is large, the ultrasonic wave is reflected by the surface of the living body. Therefore, the ultrasonic wave is not efficiently incident on the living body. For this reason, it is difficult to obtain a favorable resolution. In addition, it is desirable that ultrasonic attenuation of the acoustic lens is low in order to transmit and receive the ultrasonic wave with high sensitivity.

For this reason, a silicone resin of which the acoustic impedance is close to the acoustic impedance (in the case of a human body, $1.4 \times 10^6$ to $1.7 \times 10^6$ kg/m$^2$/sec) of a living body and which has a low ultrasonic attenuation is used as a material of the acoustic lens.

For example, JP2015-189818A discloses a composition for an ultrasound probe which contains at least three types of polyorganosiloxane mixtures containing specific branched polyorganosiloxane, and a silicone resin for an ultrasound probe obtained by vulcanizing the composition. In addition, JP2002-095081A describes an ultrasound terminal obtained by vulcanizing and molding a composition in which silicone rubber having a dimethylpolysiloxane structure containing a vinyl group is filled with a specific amount of silica particles, with a vulcanizing agent.

SUMMARY OF THE INVENTION

A resin made of silicone is soft and has a low mechanical strength. For this reason, for the purpose of improving the hardness and the mechanical strength, mixing of an inorganic filler and/or a vinyl group-containing resin (also referred to as a reinforcing agent) is performed while increasing the molecular weight of a both-terminal vinyl silicone resin. However, in a case of intending to achieve the required mechanical strength, the amount of an inorganic filler and/or vinyl group-containing resin added to the silicone resin inevitably increases. For this reason, the viscosity of the composition before the vulcanizing becomes too high. Therefore, there are problems in that a special high-torque kneading machine becomes necessary or the acoustic attenuation increases.

Therefore, development of a resin composition for an acoustic wave probe has been an important challenge which has a viscosity required at the stage before vulcanizing and satisfies all of the high resin hardness, high tear strength, and reduction in acoustic attenuation at a high level after vulcanizing.

In view of the above-described circumstances, an object of the present invention is to provide a composition for an acoustic wave probe which, before the vulcanizing, has a desired viscosity, and therefore, has excellent operability as kneading during production of a composition or molding and processing into an acoustic lens is easily performed and in which, after the vulcanizing, the acoustic impedance of the silicone resin is close to an acoustic impedance value of a living body, the acoustic attenuation is decreased, and the hardness and the tear strength can be improved.

In addition, another object of the present invention is to provide a silicone resin for an acoustic wave probe using the composition for an acoustic wave probe of the present invention, the acoustic wave probe, an ultrasound probe, an acoustic wave measurement apparatus, an ultrasound diagnostic apparatus, a photoacoustic wave measurement apparatus, and an ultrasound endoscope.

Furthermore, still another object of the present invention is to provide a composition for an acoustic wave probe and a silicone resin for an acoustic wave probe which can improve the sensitivity of the ultrasound probe, in which capacitive micromachined ultrasonic transducers (cMUT) are used as ultrasonic diagnostic transducer arrays, the photoacoustic wave measurement apparatus, and the ultrasound endoscope by using the composition for an acoustic wave probe and the silicone resin for an acoustic wave probe as constituent materials of the ultrasound probe, the photoacoustic wave measurement apparatus, and the ultrasound endoscope.

The present inventors have conducted intensive studies. As a result, they have found that the above-described problems can be solved using a vulcanizable composition which contains specific polysiloxane including polysiloxane having a vinyl group and silica particles of which the average primary particle diameter is within a specific range and which are subjected to surface treatment, and have completed the present invention based on the findings.

The above-described problems are solved by the following means.

<1> A composition for an acoustic wave probe, comprising: a polysiloxane mixture containing polysiloxane having a vinyl group, polysiloxane having two or more Si—H groups in a molecular chain, and silica particles of which an average primary particle diameter exceeds 16 nm and less than 100 nm and which are subjected to surface treatment.

<2> The composition for an acoustic wave probe according to <1>, in which 25 to 70 parts by mass of the above-described silica particles subjected to surface treatment are contained in 100 parts by mass in total of the polysiloxane mixture.

<3> The composition for an acoustic wave probe according to <1> or <2>, in which 29.9 to 74.9 parts by mass of the above-described polysiloxane having a vinyl group and 0.1 to 20 parts by mass of the above-described polysiloxane having two or more Si—H groups in a molecular chain are contained in 100 parts by mass in total of the above-described polysiloxane mixture.

<4> The composition for an acoustic wave probe according to any one of <1> to <3>, in which the above-described silica particles subjected to surface treatment are silica particles subjected to surface treatment using a silane compound.

<5> The composition for an acoustic wave probe according to <4>, in which the above-described silica particles subjected to surface treatment are silica particles subjected to surface treatment using a trimethylsilylating agent.

<6> The composition for an acoustic wave probe according to any one of <1> to <5>, in which a methanol hydrophobicity of the above-described silica particles subjected to surface treatment is 40 to 80 mass %.

<7> The composition for an acoustic wave probe according to any one of <1> to <6>, in which the above-described silica particles subjected to surface treatment are truly spherical.

<8> The composition for an acoustic wave probe according to any one of <1> to <7>, in which the above-described polysiloxane having a vinyl group has a phenyl group.

<9> The composition for an acoustic wave probe according to any one of <1> to <8>, in which a mass average molecular weight of the above-described polysiloxane having a vinyl group is 20,000 to 200,000.

<10> The composition for an acoustic wave probe according to any one of <1> to <9>, in which a mass average molecular weight of the above-described polysiloxane having a vinyl group is 40,000 to 150,000.

<11> The composition for an acoustic wave probe according to any one of <1> to <10>, in which the above-described polysiloxane having two or more Si—H groups in a molecular chain has a phenyl group.

<12> The composition for an acoustic wave probe according to any one of <1> to <11>, further comprising: 0.00001 to 0.01 parts by mass of platinum or a platinum compound with respect to 100 parts by mass of the above-described polysiloxane mixture.

<13> A silicone resin for an acoustic wave probe which is obtained by vulcanizing the composition for an acoustic wave probe according to any one of <1> to <12>.

<14> An acoustic wave probe comprising: an acoustic lens made of the silicone resin for an acoustic wave probe according to <13>; and/or an acoustic matching layer made of the silicone resin for an acoustic wave probe according to <13>.

<15> An ultrasound probe comprising: a capacitive micromachined ultrasonic transducer as an ultrasonic transducer array; and an acoustic lens containing the silicone resin for an acoustic wave probe according to <13>.

<16> An acoustic wave measurement apparatus comprising: the acoustic wave probe according to <14>.

<17> An ultrasound diagnostic apparatus comprising: the acoustic wave probe according to <14>.

<18> A photoacoustic wave measurement apparatus comprising: an acoustic lens containing the silicone resin for an acoustic wave probe according to <13>.

<19> An ultrasound endoscope comprising: an acoustic lens containing the silicone resin for an acoustic wave probe according to <13>.

Unless otherwise specified in the description of the present specification, in a case where there are groups having a plurality of the same reference numerals as each other in general formulae representing compounds, these may be the same as or different from each other, and a group (for example, an alkyl group) specified by each group may further have a substituent. In addition, the "Si—H group" means a group having three bonds on a silicon atom, but the description of the bonds is not repeated and the notation is simplified.

In addition, in the present specification, "to" means a range including numerical values denoted before and after "to" as a lower limit value and an upper limit value.

Unless otherwise specified, the mass average molecular weight in the present specification refers to a value (in terms of polystyrene) measured through gel permeation chromatography (GPC).

In view of the above-described circumstances, an object of the present invention is to provide a composition for an acoustic wave probe which has a desired viscosity and in which, after the vulcanizing, the acoustic impedance of the silicone resin is close to an acoustic impedance value of a living body, the acoustic attenuation is decreased, and the hardness and the tear strength can be improved.

In addition, another object of the present invention is to provide a silicone resin for an acoustic wave probe using the composition for an acoustic wave probe of the present invention, the acoustic wave probe, an ultrasound probe, an acoustic wave measurement apparatus, an ultrasound diagnostic apparatus, a photoacoustic wave measurement apparatus, and an ultrasound endoscope.

Furthermore, it is possible to provide an ultrasound probe in which cMUT is used as an ultrasonic diagnostic transducer array, and the silicone resin for an acoustic wave probe which can improve the sensitivity of the photoacoustic wave measurement apparatus and the ultrasound endoscope.

The above-described characteristics and advantages and other characteristics and advantages of the present invention become clearer in the following descriptions with reference to the accompanying drawing.

BRIEF DESCRIPTION OF THE DRAWING

FIG. 1 is a perspective transparent view of an example of a convex ultrasound probe which is an embodiment of an acoustic wave probe.

DESCRIPTION OF THE PREFERRED EMBODIMENTS

<<Composition for Acoustic Wave Probe>>

A composition for an acoustic wave probe (hereinafter, also simply referred to as a composition) of the present invention is a composition for an acoustic wave probe including: a polysiloxane mixture containing polysiloxane having a vinyl group, polysiloxane having two or more Si—H groups in a molecular chain, and silica particles (hereinafter, also simply referred to as silica particles) of which an average primary particle diameter exceeds 16 nm and less than 100 nm and which are subjected to surface treatment.

The content of silica particles in 100 parts by mass in total of the polysiloxane mixture is preferably 25 to 70 parts by mass, more preferably 30 to 60 parts by mass, and still more preferably 35 to 50 parts by mass. In a case where the content of the silica particles is within the above-described ranges, the tear strength, the bending durability, and the acoustic sensitivity increase.

In addition, the content of polysiloxane having a vinyl group in 100 parts by mass in total of the polysiloxane mixture is preferably 29.9 to 74.9 parts by mass. The content of polysiloxane having two or more Si—H groups in a molecular chain in 100 parts by mass in total of the polysiloxane mixture is preferably 0.1 to 20 parts by mass. The content of the polysiloxane having a vinyl group is more preferably 40 to 70 parts by mass and still more preferably 47 to 64 parts by mass. The content of the polysiloxane having two or more Si—H groups in a molecular chain is preferably 0.3 to 15 parts by mass, more preferably 0.3 to 10 parts by mass, still more preferably 0.4 to 5 parts by mass, and particularly preferably 0.4 to 3 parts by mass.

In a case where the content of the polysiloxane is within the above-described range, the hardness, the tear strength, and the acoustic impedance balance of the obtained vulcanized product (silicone resin) are excellent.

The polysiloxane mixture refers to a mixture which does not contain a catalyst for crosslinking and polymerizing (vulcanizing) the polysiloxane having a vinyl group and the polysiloxane having two or more Si—H groups in a molecular chain. Accordingly, the polysiloxane mixture contains silica particles but no catalyst.

In addition, 100 parts by mass in total of the polysiloxane mixture means that the total of the individual components contained in the polysiloxane mixture is 100 parts by mass.

Any of the above-described polysiloxanes contained in the polysiloxane mixture may be used as long as the polysiloxane has a vinyl group or two or more Si—H groups in a molecular chain. However, in the present invention, polyorganosiloxane (A) having a vinyl group and polyorganosiloxane (B) having two or more Si—H groups in a molecular chain are preferable.

Accordingly, in the present invention, a composition containing at least the polyorganosiloxane (A) having a vinyl group, the polyorganosiloxane (B) having two or more Si—H groups in a molecular chain, and silica particles (C) in a polyorganosiloxane mixture as components is preferable.

In the following detailed description, a polysiloxane mixture containing the polyorganosiloxane (A) having a vinyl group and the polyorganosiloxane (B) having two or more Si—H groups in a molecular chain will be described as a preferred embodiment.

However, each polysiloxane contained in the polysiloxane mixture is not limited to the polyorganosiloxanes (A) and (B).

<Polyorganosiloxane (A) Having Vinyl Group>

The polyorganosiloxane (A) having a vinyl group (hereinafter, also simply referred to as polyorganosiloxane (A)) used in the present invention preferably has two or more vinyl groups in a molecular chain.

Examples of the polyorganosiloxane (A) having a vinyl group include polyorganosiloxane (a) having vinyl groups at least at both terminals of a molecular chain (hereinafter, also simply referred to as polyorganosiloxane (a)) or polyorganosiloxane (b) having at least two —O—Si(CH$_3$)$_2$(CH=CH$_2$) in a molecular chain (hereinafter, also simply referred to as polyorganosiloxane (b)). Among them, the polyorganosiloxane (a) having vinyl groups at least at both terminals of a molecular chain is preferable.

The polyorganosiloxane (a) is preferably linear and the polyorganosiloxane (b) is preferably polyorganosiloxane in which —O—Si(CH$_3$)$_2$(CH=CH$_2$) is bonded to a Si atom constituting a main chain.

The polyorganosiloxane (A) having a vinyl group is subjected to hydrosilylation through a reaction with the polyorganosiloxane (B) having two or more Si—H groups in the presence of, for example, a platinum catalyst. A crosslinked (vulcanized) structure is formed through this hydrosilylation reaction (addition reaction).

The content of the vinyl group of the polyorganosiloxane (A) is not particularly limited. The content of the vinyl group is, for example, preferably 0.01 to 5 mol % and more preferably 0.05 to 2 mol % from the viewpoint of forming a sufficient network between components contained in a composition for an acoustic wave probe.

Here, the content of the vinyl group is represented by mol % of the vinyl group-containing siloxane unit based on 100 mol % of all the units constituting the polyorganosiloxane (A). One vinyl group-containing siloxane unit has 1 to 3 vinyl groups. Among them, one vinyl group is preferable for one vinyl group-containing siloxane unit. For example, in a case where all Si atoms of Si in a Si—O unit and at a terminal which constitute a main chain have at least one vinyl group, the content becomes 100 mol %.

In addition, the polyorganosiloxane (A) preferably has a phenyl group, and the content of the phenyl group of the polyorganosiloxane (A) is not particularly limited. The content of the phenyl group is, for example, preferably 1 to 80 mol % and preferably 2 to 40 mol % from the viewpoint of mechanical strength in a case where a silicone resin for an acoustic wave probe is made.

Here, the content of the phenyl group is represented by mol % of the phenyl group-containing siloxane unit based on 100 mol % of all the units constituting the polyorganosiloxane (A). One phenyl group-containing siloxane unit has 1 to 3 phenyl groups. Among them, two phenyl groups are preferable for one phenyl group-containing siloxane unit. For example, in a case where all Si atoms of Si in a Si—O unit and at a terminal which constitute a main chain have at least one phenyl group, the content becomes 100 mol %.

The "unit" refers to Si atoms in a Si—O unit and at a terminal which constitute a main chain.

The degree of polymerization and the specific gravity are not particularly limited. The degree of polymerization is preferably 200 to 3,000 and more preferably 400 to 2,000, and the specific gravity is preferably 0.9 to 1.1 from the viewpoint of improving the mechanical strength, the hardness, the chemical stability, and the like of an obtained silicone resin for an acoustic wave probe (hereinafter, also simply referred to as a silicone resin).

The mass average molecular weight of the polyorganosiloxane having a vinyl group is preferably 20,000 to 200,000, more preferably 40,000 to 150,000, and still more preferably 45,000 to 120,000 from the viewpoints of the mechanical strength, the hardness, and/or easiness of processing.

The mass average molecular weight can be measured using, for example, TOLUENE (manufactured by Shonan Wako Junyaku K.K.) as an eluent, TSKgel (registered trademark), G3000HXL+TSKgel (registered trademark), and G2000HXL as columns, and a RI detector under the conditions of a temperature of 23° C. and a flow rate of 1 mL/min after preparing a GPC apparatus HLC-8220 (manufactured by TOSOH CORPORATION).

The kinematic viscosity at 25° C. is preferably $1\times10^{-5}$ to 10 m$^2$/s, more preferably $1\times10^{-4}$ to 1 m$^2$/s, and still more preferably $1\times10^{-3}$ to 0.5 m$^2$/s.

The kinematic viscosity can be measured and obtained at a temperature of 25° C. using a Ubbelohde-type viscometer (for example, a trade name of SU manufactured by SIBATA SCIENTIFIC TECHNOLOGY LTD.) in compliance with JIS Z8803.

Polyorganosiloxane represented by General Formula (A) is preferable as the polyorganosiloxane (a) having vinyl groups at least at both terminals of a molecular chain.

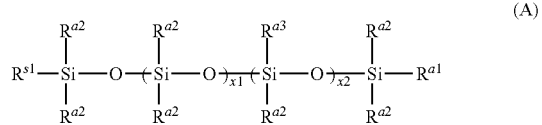

In General Formula (A), $R^{a1}$ represents a vinyl group and $R^{a2}$ and $R^{a3}$ each independently represent an alkyl group, a cycloalkyl group, an alkenyl group, or an aryl group. x1 and x2 each independently represent an integer of 1 or more. Here, a plurality of $R^{a2}$'s and a plurality of $R^{a3}$'s may be the same as or different from each other. In addition, each of the groups of $R^{a2}$ and $R^{a3}$ may further have a substituent.

The number of carbon atoms in an alkyl group in $R^{a2}$ and $R^{a3}$ is preferably 1 to 10, more preferably 1 to 4, still more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group in $R^{a2}$ and $R^{a3}$ is preferably 3 to 10, more preferably 5 to 10, and still more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group in $R^{a2}$ and $R^{a3}$ is preferably 2 to 10, more preferably 2 to 4, and still more preferably 2. Examples of the alkenyl group include a vinyl group, an allyl group, and a butenyl group.

The number of carbon atoms in an aryl group in $R^{a2}$ and $R^{a3}$ is preferably 6 to 12, more preferably 6 to 10, and still more preferably 6 to 8. Examples of the aryl group include a phenyl group, a tolyl group, and a naphthyl group.

The alkyl group, the cycloalkyl group, the alkenyl group, and the aryl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a2}$ and $R^{a3}$ are preferably an alkyl group, an alkenyl group, or an aryl group, more preferably an alkyl group having 1 to 4 carbon atoms, a vinyl group, or a phenyl group, and still more preferably a methyl group, a vinyl group, or a phenyl group.

Among them, $R^{a2}$ is preferably a methyl group. $R^{a3}$ is preferably a methyl group, a vinyl group, or a phenyl group, more preferably a methyl group or a phenyl group, and particularly preferably a phenyl group. In addition, it is also preferable that both $R^{a2}$'s in the repetition of x1 are phenyl groups.

x1 is preferably an integer of 200 to 3,000 and more preferably an integer of 400 to 2,000.

x2 is preferably an integer of 1 to 3,000, more preferably an integer of 1 to 1,000, still more preferably an integer of 40 to 1,000, and particularly preferably an integer of 40 to 700.

In addition, as another embodiment, x1 is preferably an integer of 1 to 3,000 and more preferably an integer of 5 to 1,000.

Examples of the polyorganosiloxane having vinyl groups at least at both terminals of a molecular chain include DMS series (for example, DMS-V31, DMS-V31S15, DMS-V33, DMS-V35, DMS-V35R, DMS-V41, DMS-V42, DMS-V46, DMS-V51, and DMS-V52), and PDV series (for example, PDV-0341, PDV-0346, PDV-0535, PDV-0541, PDV-1631, PDV-1635, PDV-1641, and PDV-2335), PMV-9925, PVV-3522, FMV-4031, and EDV-2022 all of which are trade names manufactured by GELEST, INC.

In the DMS-V31S15, fumed silica is formulated into DMS-V31S15 in advance, and therefore, kneading using a special device is unnecessary.

The polyorganosiloxane (A) having a vinyl group in the present invention may be used singly or in a combination of two or more thereof.

<Polyorganosiloxane (B) Having Two or More Si—H Groups in Molecular Chain>

The polyorganosiloxane (B) having two or more Si—H groups in a molecular chain used in the present invention (hereinafter, also simply referred to as polyorganosiloxane (B)) has two or more Si—H groups in a molecular chain.

In a case where there are two or more Si—H groups in a molecular chain, it is possible to crosslink polyorganosiloxane having at least two polymerizable unsaturated groups.

There is a linear structure and a branched structure in the polyorganosiloxane (B), and the linear structure is preferable.

The mass average molecular weight of a linear structure is preferably 500 to 100,000 and more preferably 1,500 to 50,000 from the viewpoints of the mechanical strength and the hardness.

The polyorganosiloxane (B) which has a linear structure and two or more Si—H groups in a molecular chain is preferably polyorganosiloxane represented by General Formula (B).

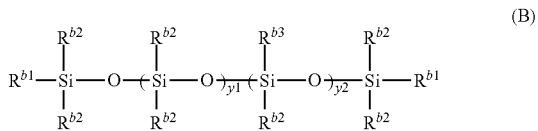

(B)

In General Formula (B), $R^{b1}$ to $R^{b3}$ each independently represent a hydrogen atom, an alkyl group, a cycloalkyl group, an alkenyl group, an aryl group, or —O—Si($R^{b5}$)$_2$($R^{b4}$). $R^{b4}$ and $R^{b5}$ each independently represent a hydrogen atom, an alkyl group, a cycloalkyl group, an alkenyl group, or an aryl group. y1 and y2 each independently represent an integer of 1 or more. Here, a plurality of $R^{b1}$'s, a plurality of $R^{b2}$'s a plurality of $R^{b3}$'s, a plurality of $R^{b4}$'s, and a plurality of $R^{b5}$'s each may be the same as or different from each other. In addition, each of the groups of $R^{b1}$ to $R^{b5}$ may further be substituted with a substituent. However, there are two or more Si—H groups in a molecular chain.

An alkyl group, a cycloalkyl group, an alkenyl group, and an aryl group in $R^{b1}$ to $R^{b3}$ are synonymous with an alkyl group, a cycloalkyl group, an alkenyl group, and an aryl group in $R^{a2}$ and $R^{a3}$, and preferred ranges thereof are also the same as each other.

An alkyl group, a cycloalkyl group, an alkenyl group, and an aryl group in $R^{b4}$ and $R^{b5}$ of —O—Si($R^{b5}$)$_2$($R^{b4}$) are synonymous with an alkyl group, a cycloalkyl group, an alkenyl group, and an aryl group in $R^{b1}$ to $R^{b3}$, and preferred ranges thereof are also the same as each other.

$R^{b1}$ to $R^{b3}$ are preferably a hydrogen atom, an alkyl group, an alkenyl group, an aryl group, or —O—Si($R^{b5}$)$_2$($R^{b4}$), and more preferably a hydrogen atom, an alkyl group having 1 to 4 carbon atoms, a vinyl group, a phenyl group, or —O—Si (CH$_3$)$_2$H.

Among them, $R^{b1}$ and $R^{b2}$ are preferably a hydrogen atom, an alkyl group, an alkenyl group, or an aryl group, more preferably a hydrogen atom or an alkyl group, and still more preferably a hydrogen atom or a methyl group.

$R^{b3}$ is preferably a hydrogen atom, an alkyl group, an alkenyl group, an aryl group, or —O—Si($R^{b5}$)$_2$($R^{b4}$), more preferably a hydrogen atom or an aryl group, and still more preferably a hydrogen atom or a phenyl group.

In the present invention, in a case where $R^{b3}$ is a phenyl group, it is preferable that $R^{b1}$ is a hydrogen atom. It is more preferable that $R^{b1}$ is a hydrogen atom and the following conditions are satisfied.

1) One $R^{b2}$ in the repetition of y1 is a hydrogen atom and the remaining $R^{b2}$ is an alkyl group, $R^{b2}$ in the repetition of y2 is an alkyl group, and $R^{b3}$ is a phenyl group.

2) y1 is 0, $R^{b2}$ in the repetition of y2 is an alkyl group, and $R^{b3}$ is a phenyl group.

3) y1 is 0, $R^{b2}$ in the repetition of y2 is —O—Si($R^{b5}$)$_2$($R^{b4}$), and $R^{b3}$ is a phenyl group.

In the above-described 3), a case where $R^{b4}$ is a hydrogen atom and $R^{b5}$ is an alkyl group is particularly preferable.

y1 is preferably an integer of 0 to 2,000, more preferably an integer of 0 to 1,000, and still more preferably an integer of 0 to 30.

y2 is preferably an integer of 1 to 2,000, more preferably an integer of 1 to 1,000, and still more preferably an integer of 1 to 30.

y1+y2 is preferably an integer of 5 to 2,000, more preferably an integer of 7 to 1,000, still more preferably an integer of 10 to 50, and particularly preferably an integer of 15 to 30.

As a combination of $R^{b1}$ to $R^{b3}$, a combination of a hydrogen atom or an alkyl group having 1 to 4 carbon atoms as $R^{b1}$, an alkyl group having 1 to 4 carbon atoms as $R^{b2}$, and a hydrogen atom as $R^{b3}$ is preferable and a combination of an alkyl group having 1 to 4 carbon atoms as $R^{b1}$, an alkyl group having 1 to 4 carbon atoms as $R^{b2}$, and a hydrogen atom as $R^{b3}$ is more preferable.

In the preferred combinations, the content of a hydrosilyl group represented by y2/(y1+y2) is preferably greater than 0.1 and less than or equal to 1.0 and more preferably greater than 0.2 and less than or equal to 1.0.

Examples of the polyorganosiloxane (B) with a linear structure include HMS-064 (MeHSiO: 5 to 7 mol %), HMS-082 (MeHSiO: 7 to 8 mol %), HMS-301 (MeHSiO: 25 to 30 mol %), and HMS-501 (MeHSiO: 50 to 55 mol %) as methylhydrosiloxane-dimethylsiloxane copolymers (trimethylsiloxane terminated), HPM-502 (MeHSiO: 45 to 50 mol %) as a methylhydrosiloxane-phenylmethylsiloxane copolymer, and HMS-991 (MeHSiO: 100 mol %) as a methylhydrosiloxane polymer, all of which are trade names of GELEST, INC.

Here, the mol % of MeHSiO has the same meaning as that y2/(y1+y2) in the above-described preferred combination of $R^{b1}$ to $R^{b3}$ is multiplied by 100.

It is preferable that both the linear structure and the branched structure have no vinyl group from the viewpoint of preventing the progress of a cross-linking reaction within a molecule. Among these, it is preferable that the branched structure has no vinyl group.

The polyorganosiloxane (B), which has a branched structure and two or more Si—H groups in a molecular chain, has a branched structure and two or more hydrosilyl groups (Si—H groups).

The specific gravity is preferably 0.9 to 0.95.

The polyorganosiloxane (B) with a branched structure is preferably represented by Average Composition Formula (b).

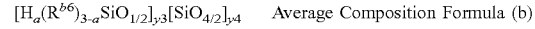

$[H_a(R^{b6})_{3-a}SiO_{1/2}]_{y3}[SiO_{4/2}]_{y4}$   Average Composition Formula (b)

Here, $R^{b6}$ represents an alkyl group, a cycloalkyl group, an alkenyl group, or an aryl group, a represents 0.1 to 3, and y3 and y4 each independently represent an integer of 1 or more.

An alkyl group, a cycloalkyl group, an alkenyl group, and an aryl group in $R^{b6}$ are synonymous with an alkyl group, a cycloalkyl group, an alkenyl group, and an aryl group in $R^{a2}$ and $R^{a3}$, and preferred ranges thereof are also the same as each other.

a is preferably 1.

The content of a hydrosilyl group represented by a/3 is preferably greater than 0.1 and less than 0.6 and more preferably greater than 0.1 and less than 0.4.

In contrast, in a case of representing the polyorganosiloxane (B) with a branched structure using a chemical structural formula, polyorganosiloxane in which —O—Si(CH$_3$)$_2$(H) is bonded to a Si atom constituting a main chain is preferable and polyorganosiloxane having a structure represented by General Formula (Bb) is more preferable.

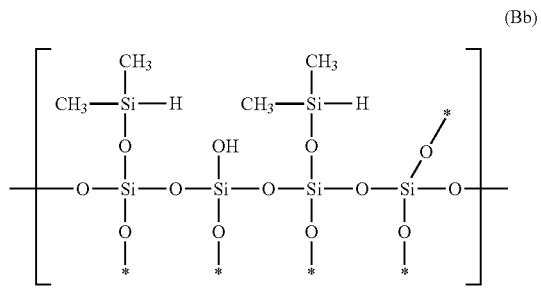

(Bb)

In General Formula (Bb), * means a bond with at least a Si atom of siloxane.

Examples of the polyorganosiloxane (B) with a branched structure include HQM-107 (trade name of Hydride Q Resin manufactured by GELEST, INC.) and HDP-111 (trade name of polyphenyl-(dimethylhydroxy)siloxane (hydride terminated), [(HMe$_2$SiO)(C$_6$H$_5$Si)O]: 99 to 100 mol % manufactured by GELEST, INC.)

The polyorganosiloxane (B) having two or more Si—H groups in a molecular chain used in the present invention may be used singly, or in a combination of two or more thereof. In addition, the polyorganosiloxane (B) with a linear structure and the polyorganosiloxane (B) with a branched structure may be used in combination.

<Silica Particles (C)>

The silica particles (C) used in the present invention are silica particles of which an average primary particle diameter exceeds 16 nm and less than 100 nm and which are subjected to surface treatment.

An effect of improving the acoustic impedance, the hardness, and the mechanical strength of a silicone resin is obtained by adding silica particles to the silicone resin. However, the acoustic attenuation increases with an increase in the amount of the silica particles added, and in a case where the addition amount is too large, the viscosity of the composition for an acoustic wave probe before vulcanizing increases.

However, in the present invention, it is considered that, in a case where the silica particles (C) subjected to surface treatment which have a particle diameter within a specific range are used, it is possible to reduce the acoustic attenuation and reduce the viscosity before vulcanizing. The reason for this is not yet certain, but it is presumed as follows.

That is, in a case where silica particles having a small average primary particle diameter are used, the tear strength of the silicone resin is improved and increase in the acoustic attenuation is suppressed, whereas the viscosity of the composition for an acoustic wave probe before vulcanizing increases. In the present invention, by subjecting surface treatment on silica particles having an average primary particle diameter within the above-described specific range, an interaction with polyorganosiloxane becomes stronger and the affinity increases. For this reason, it is considered that aggregation of silica particles having a small average primary particle diameter is suppressed, the viscosity of the composition for an acoustic wave probe before vulcanizing is suppressed, the tear strength of the silicone resin after vulcanizing is high, and the acoustic attenuation is decreased.

The average primary particle diameter of the silica particles (C) used in the present invention is greater than 16 nm and less than 100 nm, preferably 18 nm to 90 nm, more preferably 20 nm to 80 nm, and still more preferably 25 nm to 70 nm from the viewpoints of suppressing increase in the viscosity of the composition for an acoustic wave probe before vulcanizing, suppressing increase in the acoustic attenuation of the silicone resin, and improving the tear strength.

Here, the average primary particle diameter means a volume average particle diameter. The volume average particle diameter can be obtained by, for example, measuring the particle diameter distribution using a laser diffraction scattering type particle diameter distribution measurement apparatus (for example, trade name "LA910" manufactured by HORIBA, Ltd.). In the present specification, for silica particles of which the average primary particle diameter has not been disclosed in the catalog or for silica particles newly manufactured, the average primary particle diameter is obtained through the above-described measurement method.

Here, the average primary particle diameter of the silica particles (C) means an average primary particle diameter in a state in which the surface treatment has been performed.

The silica particles (C) may be used singly or in a combination of two or more thereof.

The specific surface area of the silica particles (C) used in the present invention is preferably 1 to 400 m$^2$/g, more preferably 5 to 200 m$^2$/g, and particularly preferably 10 to 100 m$^2$/g from the viewpoint of improving the hardness and/or the mechanical strength of a silicone resin to be obtained.

The silica particles (C) used in the present invention are silica particles whose surface has been treated, and preferably silica particles subjected to surface treatment with a silane compound.

A usual technique may be used as a technique of the surface treatment. Examples of the technique of the surface treatment using a silane compound include a technique of performing surface treatment using a silane coupling agent and a technique of performing coating using a silicone compound.

(i) Silane Coupling Agent

A silane coupling agent having a hydrolyzable group is preferable as a silane coupling agent from the viewpoint of improving the hardness and/or the mechanical strength of a silicone resin. Surface modification of silica particles is performed such that a hydrolyzable group in a silane coupling agent becomes a hydroxyl group after being hydrolyzed using water and this hydroxyl group is subjected to a dehydration and condensation reaction with a hydroxyl group on the surfaces of the silica particles, thereby improving the hardness and/or the mechanical strength of an obtained silicone resin. Examples of the hydrolyzable group include an alkoxy group, an acyloxy group, and a halogen atom.

In a case where the surfaces of silica particles are hydrophobically modified, affinity between the silica particles (C) and the polyorganosiloxanes (A) and (B) becomes favorable, and therefore, the hardness and the mechanical strength of an obtained silicone resin are improved, which is preferable.

Examples of a silane coupling agent having a hydrophobic group as a functional group include alkoxysilanes such as methyltrimethoxysilane (MTMS), dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyl triethoxysilane, and decyltrimethoxysilane; chlorosilanes such as methyltrichlorosilane, dimethyldichlorosilane, trimethylchlorosilane, and phenyltrichlorosilane; and hexamethyldisilazane (HMDS).

In addition, examples of a silane coupling agent having a vinyl group as a functional group include alkoxysilanes such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane and vinylmethyldichlorosilane; and divinyltetramethyldisilazane.

Silica particles treated with a trialkylsilylating agent are preferable and silica particles treated with a trimethylsilylating agent are more preferable as the silica particles (C) subjected to surface treatment with a silane coupling agent.

Examples of the silane compound include the above-described silane coupling agents and a silane coupling agent in which a functional group in a silane coupling agent is substituted with an alkyl group.

In addition, examples of the trimethylsilylating agent include trimethylchlorosilane and hexamethyldisilazane (HMDS) described in the above-described silane coupling agent, and methyltrimethoxysilane (MTMS) and trimethylmethoxysilane which are silane coupling agents in which a functional group is substituted with an alkyl group.

Examples of a commercially available silane coupling agent include hexamethyldisilazane (HMDS) (trade name: HEXAMETHYLDISILAZANE (SIH6110.1) manufactured by GELEST, INC.) A hydroxyl group existing on the surfaces of silica particles is covered with a trimethylsilyl group through a reaction with hexamethyldisilazane (HMDS), methyltrimethoxysilane (MTMS), trimethylmethoxysilane, and the like and the surfaces of the silica particles are hydrophobically modified.

In the present invention, the silane coupling agent may be used alone or in a combination of two or more thereof.

(ii) Silicone Compound

A silicone compound with which the silica particles (C) are coated may be a polymer formed through siloxane bonding.

Examples of the silicone compound include a silicone compound in which all or a part of side chains and/or terminals of polysiloxane has become a methyl group, a silicone compound in which a part of a side chain is a hydrogen atom, a modified silicone compound in which organic groups such as an amino group and/or an epoxy group is introduced into all or a part of side chains and/or terminals, and a silicone resin having a branched structure. The silicone compound may be either of a linear structure or a cyclic structure.

Examples of the silicone compound in which all or a part of side chains and/or terminals of polysiloxane has become a methyl group include monomethylpolysiloxane such as polymethylhydrosiloxane (hydride terminated), polymethylhydrosiloxane (trimethylsiloxy terminated), polymethylphenylsiloxane (hydride terminated), and polymethylphenylsiloxane (trimethylsiloxy terminated); and dimethylpolysiloxanes such as dimethylpolysiloxane (hydride terminated), dimethylpolysiloxane (trimethylsiloxy terminated), and cyclic dimethylpolysiloxane.

Examples of the silicone compound in which a part of side chains is a hydrogen atom include methylhydrosiloxane-dimethylsiloxane copolymer (trimethylsiloxy terminated), methylhydrosiloxane-dimethylsiloxane copolymer (hydride terminated), polymethylhydrosiloxane (hydride terminated), polymethylhydrosiloxane (trimethylsiloxy terminated), polyethylhydrosiloxane (triethylsiloxy terminated), polyphenyl-(dimethylhydrosiloxy) siloxane (hydride terminated), methylhydrosiloxane-phenylmethylsiloxane copolymer (hydride terminated), methylhydrosiloxane-octylmethylsiloxane copolymer, and methylhydrosiloxane-octylmethylsiloxane terpolymer.

In addition, examples of modified silicone into which an organic group is introduced include reactive silicone into which an amino group, an epoxy group, a methoxy group, a (meth)acryloyl group, a phenol group, a carboxylic anhydride group, a hydroxy group, a mercapto group, a carboxyl group, and/or an organic group of a hydrogen atom are introduced; and non-reactive silicone modified with polyether, aralkyl, fluoroalkyl, long chain alkyl, long chain aralkyl, higher fatty acid ester, higher fatty acid amide, and/or polyether methoxy.

Silica particles coated with a silicone compound can be obtained through a usual method. For example, the silica particles can be obtained by being mixed and stirred in dimethylpolysiloxane for a certain period of time and being filtered.

In addition, in a case of using reactive modified silicone as a silicone compound, surface modification of silica particles is performed through reaction of an organic group with a hydroxyl group of the surfaces of the silica particles, and therefore, the hardness and/or the mechanical strength of an obtained silicone resin is improved.

An Example of the commercially available silicone compound includes methyl hydrogen silicone oil (MHS) (trade name: KF-99, manufactured by Shin-Etsu Chemical Co., Ltd.) which is polymethylhydrosiloxane (trimethylsiloxy terminated).

The methanol hydrophobicity of the silica particles (C) which is calculated through the following methanol titration test is preferably 40 to 80 mass %, more preferably 50 to 80 mass %, and still more preferably 60 to 80 mass %. Here, the larger the methanol hydrophobicity, the higher the hydrophobicity, and the smaller the methanol hydrophobicity, the higher the hydrophilicity.

50 ml of ion exchange water and 0.2 g of silica particles as samples are placed in a beaker at 25° C. and stirred with a magnetic stirrer, methanol is added dropwise thereto from a burette, and the amount (Xg) of methanol added dropwise until the whole sample settles is measured. The methanol hydrophobicity is calculated using the following equation.

$$\text{Methanol hydrophobicity(mass \%)} = X/(50+X) \times 100$$

In a case where the methanol hydrophobicity is within the above-described preferred ranges, it is possible to suppress decrease in acoustic sensitivity in a case where a silicone resin for an acoustic wave probe is obtained without increase in the viscosity of the composition for an acoustic wave probe before vulcanizing.

The Wardell's sphericity of a primary particle of the silica particles (C) is preferably 0.7 to 1, more preferably 0.8 to 1, and still more preferably 0.9 to 1.

Here, the "Wardell's sphericity" (refer to Chemical Engineering Handbook published by Maruzen Inc.) is an index obtained by measuring the sphericity of a particle as (diameter of circle equal to projection area of particle)/(diameter of minimum circle circumscribing projection image of particle). A particle having the index closer to 1.0 means a particle closer to a true sphere.

It is possible to use, for example, a scanning electron microscope (SEM) photograph can be used to measure the Wardell's sphericity (hereinafter, also simply referred to as sphericity). Specifically, for example, about 100 primary particles are observed using the SEM photograph, and each sphericity thereof is calculated. An average value obtained by dividing the total of the calculated sphericities by the number of observed primary particles is regarded as the sphericity.

In a case where the Wardell's sphericity is within the above-described preferred ranges, it is considered that the acoustic sensitivity is improved because the area of the acoustic wave hitting the silica particles becomes smaller in a case where the silicone resin is irradiated with the acoustic wave. In particular, it is considered that the acoustic sensitivity is more effectively improved in a case where the shapes of the silica particles (C) are truly spherical within a specific range of the average primary particle diameter of the silica particle (C) of the present invention.

In this specification, the "true spherical shape" also includes a slightly distorted sphere of which the Wardell's sphericity is within a range of 0.9 to 1.

The silica particles are roughly classified into combustion method silica (that is, fumed silica) obtained by burning a silane compound, deflagration method silica obtained by explosively burning metallic silicon powder, wet-type silica (among which silica synthesized under alkaline conditions is referred to as precipitation method silica and silica synthesized under acidic conditions is referred to as gel method silica) obtained through a neutralization reaction with sodium silicate and mineral acid, and sol-gel method silica (so-called Stoeber method) obtained through hydrolysis of hydrocarbyloxysilane depending on its production method.

Preferred examples of a method for producing truly spherical silica particles include an explosion method and a sol-gel method.

The sol-gel method is a method of obtaining hydrophilic spherical silica particles essentially consisting of $SiO_2$ units by hydrolyzing and condensing a hydrocarbyloxysilane (preferably tetrahydrocarbyloxysilane) or a partial hydrolytic condensation product thereof or a combination thereof.

In addition, the hydrophobic treatment of the surfaces of the silica particles can also be carried out by introducing $R^3{}_3Si_{1/2}$ units ($R^3$'s are the same as or different from each other and are substituted or unsubstituted monovalent hydrocarbon groups having 1 to 20 carbon atoms) onto the surfaces of hydrophilic spherical silica particles.

Specifically, the hydrophobic treatment thereof can be carried out, for example, through methods disclosed in JP2007-99582A and JP2014-114175A.

In general, the vinyl group possessed by the polyorganosiloxane (A) and the Si—H group possessed by the polyorganosiloxane (B) stoichiometrically react with each other in a ratio of 1:1.

However, the equivalent of the Si—H group possessed by the polyorganosiloxane (B) to the vinyl group possessed by the polyorganosiloxane (A) from the viewpoint of a reaction between all the vinyl groups with the Si—H groups is preferably vinyl group: Si—H group=1:1.1 to 1:8 and more preferably 1:1.2 to 1:5.

<Other Components>

In the composition for an acoustic wave probe of the present invention, it is possible to appropriately formulate a platinum catalyst for an addition polymerization reaction, a vulcanization retardant, a solvent, a dispersant, a pigment, a dye, an antistatic agent, an antioxidant, a flame retardant, and/or a thermal conductivity enhancer in addition to the polyorganosiloxane (A) having a vinyl group, the polyorganosiloxane (B) having two or more Si—H groups in a molecular chain, and the silica particles (C).

—Catalyst—

Examples of the catalyst include platinum or a platinum-containing compound (hereinafter, also simply referred to as a platinum compound). Any platinum or platinum compound can be used.

Specific examples thereof include a catalyst in which platinum black or platinum is carried on an inorganic compound, carbon black, or the like; platinum chloride or an alcohol solution of platinum chloride; a complex salt of platinum chloride and olefin; and a complex salt of platinum chloride and vinyl siloxane. The catalyst may be used singly, or in a combination of two or more thereof.

The catalyst is necessary in the hydrosilylation reaction in which the Si—H group of the polyorganosiloxane (B) is added to the vinyl group of the polyorganosiloxane (A). The polyorganosiloxane (A) is cross-linked by the polyorganosiloxane (B) due to progress of a hydrosilylation reaction (addition vulcanization reaction) to form a silicone resin.

Here, the catalyst may be contained in the composition for an acoustic wave probe of the present invention or may be brought into contact with the composition for an acoustic wave probe without being contained in the composition for an acoustic wave probe. The latter case is preferable.

Examples of commercially available platinum catalyst include platinum compounds (a trade name of PLATINUM CYCLOVINYLMETHYLSILOXANE COMPLEX IN CYCLIC METHYLVINYLSILOXANES (SIP6832.2) with 2 mass % of Pt concentration; and a trade name of PLATINUM DIVINYLTETRAMETHYLDISILOXANE COMPLEX IN VINYL-TERMINATED POLYDIMETHYLSILOXANE (SIP6830.3) with 3 mass % of Pt concentration, all of which are manufactured by GELEST, INC.)

In a case where a catalyst is contained in the composition for an acoustic wave probe of the present invention, the content of the catalyst present with respect to 100 parts by mass of a polysiloxane mixture is not particularly limited, but is preferably 0.00001 to 0.05 parts by mass, more preferably 0.00001 to 0.01 parts by mass, still more preferably 0.00002 to 0.01 parts by mass, and particularly preferably 0.00005 to 0.005 parts by mass from the viewpoint of reactivity.

In addition, it is possible to control the vulcanization temperature by selecting an appropriate platinum catalyst. For example, platinum-vinyldisiloxane is used for room temperature vulcanization (RTV) at lower than or equal to 50° C. and platinum-cyclic vinylsiloxane is used for high temperature vulcanization (HTV) at higher than or equal to 130° C.

—Vulcanization Retardant—

In the present invention, a vulcanization retardant for vulcanization reaction can be appropriately used. The vulcanization retardant is used for delaying the above-described addition vulcanization reaction and examples thereof include a low molecular weight vinylmethylsiloxane homopolymer (trade name: VMS-005 manufactured by GELEST, INC.)

The vulcanization rate, that is, the working time can be adjusted depending on the content of the vulcanization retardant.

[Viscosity of Composition for Acoustic Wave Probe Before Vulcanizing]

The viscosity of the composition for an acoustic wave probe before performing a vulcanization reaction is preferably low. In a case where the viscosity is too high, it becomes difficult to prepare a composition for an acoustic wave probe in which the silica particles (C) are dispersed through kneading. The viscosity of the composition for an acoustic wave probe before adding a catalyst which initiates the vulcanization reaction is measured in order to measure the viscosity before vulcanizing. Specifically, the viscosity can be measured under the following conditions.

The viscosity of the composition for an acoustic wave probe before addition of a platinum catalyst is measured using a viscosity/viscoelasticity measurement apparatus (for example, trade name "RheoStress RS6000" manufactured by HAAKE) under the conditions of a temperature of 23° C. and a shear rate of $0.001$ $s^{-1}$.

The viscosity (at 23° C.) measured under the above-described conditions is preferably less than or equal to 5,000 Pa·s, more preferably less than or equal to 1,000 Pa·s, and particularly preferably less than or equal to 200 Pa·s. The realistic lower limit value is greater than or equal to 10 Pa·s.

In a case where the viscosity is within the above-described preferred ranges, the composition for an acoustic wave probe can be easily handled during processing. In addition, since residual air bubbles in the composition for an acoustic wave probe can be suppressed, an increase in acoustic attenuation caused by air bubbles in the silicone resin for an acoustic wave probe can also be suppressed.

<Method for Producing Composition for Acoustic Wave Probe and Silicone Resin for Acoustic Wave Probe>

The composition for an acoustic wave probe of the present invention can be produced through any method.

For example, the composition for an acoustic wave probe can be obtained by kneading components constituting the composition for an acoustic wave probe using a kneader, a pressure kneader, a Banbury mixer (continuous kneader), and a kneading device with two rolls. The order of mixing the components is not particularly limited.

It is preferable to first make a polyorganosiloxane mixture in which the silica particles (C) are dispersed in the polyorganosiloxane (A) having a vinyl group and the polyorganosiloxane (B) having two or more Si—H groups in a molecular chain, from the viewpoint of obtaining a homogeneous composition. Thereafter, it is possible to produce a composition for an acoustic wave probe after adding a catalyst to the polyorganosiloxane mixture, in which the silica particles (C) are dispersed, and performing defoamation under reduced pressure.

The kneading conditions of the polyorganosiloxane mixture in which the silica particles (C) are dispersed are not particularly limited as long as the silica particles (C) are dispersed. For example, the polyorganosiloxane mixture is preferably kneaded at 10° C. to 50° C. for 1 to 72 hours.

It is possible to obtain a silicone resin for an acoustic wave probe of the present invention by vulcanizing the composition for an acoustic wave probe of the present invention which has been obtained in this manner. Specifically, it is possible to obtain a silicone resin for an acoustic wave probe by, for example, thermally vulcanizing the composition for an acoustic wave probe for 5 minutes to 500 minutes at 20° C. to 200° C.

<Mechanical Strength and Acoustic Characteristics of Silicone Resin>

The silicone resin for an acoustic wave probe of the present invention is obtained by vulcanizing the composition for an acoustic wave probe of the present invention. That is, the polyorganosiloxane (A) in the composition for an acoustic wave probe of the present invention is cross-linked with the polyorganosiloxane (B) through the above-described addition vulcanization reaction.

Hereinafter, the mechanical strength and the acoustic characteristics of a silicone resin will be described in detail.

Here, ultrasonic characteristics among the acoustic characteristics will be described. However, the acoustic characteristics are not limited to the ultrasonic characteristics, and relates to acoustic characteristics at an appropriate frequency which is selected in accordance with a test object, measurement conditions, and the like.

[Hardness]

The type A durometer hardness of a silicone resin sheet with a thickness of 2 mm is measured using a rubber hardness meter (for example, trade name "RH-201A" manufactured by Excel co., Ltd.) in compliance with JIS K6253-3 (2012).

The hardness is preferably greater than or equal to 15, more preferably greater than or equal to 25, and still more preferably greater than or equal to 40 from the viewpoint of preventing deformation in a case where the silicone resin sheet is incorporated into an acoustic wave probe as a part of the acoustic wave probe. A practical upper limit value is less than or equal to 90.

[Tear Strength Test]

A trouser-type test piece of a silicone resin sheet with a thickness of 2 mm is manufactured and the tear strength is measured in compliance with JIS K6252 (2007).

The tear strength is preferably greater than or equal to 7 N/cm and more preferably greater than or equal to 10 N/cm. A practical upper limit value is less than or equal to 150 N/cm.

[Acoustic Impedance]

The density of a silicone resin sheet with a thickness of 2 mm at 25° C. is measured using an electronic gravimeter (for example, a trade name of "SD-200L" manufactured by ALFA MIRAGE) in accordance with a density measurement method of a method A (underwater substitution method) disclosed in JIS K7112 (1999). The acoustic velocity of an acoustic wave is measured at 25° C. using a sing-around type acoustic velocity measurement apparatus (for example, a trade name of "UVM-2 type" manufactured by Ultrasonic Engineering Co., Ltd.) in compliance with JIS Z2353 (2003) and acoustic impedance is obtained from a sum of the density and the acoustic velocity which had been measured.

[Acoustic (Ultrasonic) Attenuation and Sensitivity]

A sinusoidal signal (a wave) of 5 MHz which had been output from an ultrasound oscillator (for example, a function generator with a trade name of "FG-350" manufactured by IWATSU ELECTRIC CO., LTD.) is input into an ultrasound probe (for example, manufactured by JAPAN PROBE), and an ultrasound pulse wave with a center frequency of 5 MHz is generated in water from the ultrasound probe. The magnitude of the amplitude before and after the generated ultrasonic wave passed through a silicone resin sheet with a thickness of 2 mm is measured in a water temperature environment of 25° C. using an ultrasound receiver (for example, an oscilloscope with a trade name of "VP-5204A" manufactured by Matsushita Electric Industrial Co., Ltd.) The acoustic (ultrasonic) attenuations of each sheet are compared with each other by comparing the acoustic (ultrasonic) sensitivities of each sheet with each other.

The acoustic (ultrasonic) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained when the ultrasound oscillator receives an acoustic wave (ultrasonic wave) that the acoustic wave (ultrasonic wave) generated passes through a sheet and is reflected from an opposite side of the sheet.

Acoustic(Ultrasonic)sensitivity=20×Log($Vs/Vin$)

In an evaluation system in the present invention, the acoustic (ultrasonic) sensitivity is preferably greater than or equal to −70.0 dB.

The composition for an acoustic wave probe of the present invention is useful for medical members and can preferably be used, for example, in an acoustic wave probe or an acoustic wave measurement apparatus. The acoustic wave measurement apparatus of the present invention is not limited to an ultrasound diagnostic apparatus or a photoacoustic wave measurement apparatus, and is referred to as an apparatus that receives an acoustic wave which has been reflected or generated from an object and displays the received acoustic wave as an image or a signal strength.

Particularly, the composition for an acoustic wave probe of the present invention can suitably be used in: a material of an acoustic matching layer which is provided in an acoustic lens of an ultrasound diagnostic apparatus or between a piezoelectric element and the acoustic lens and plays a role of matching acoustic impedance between the piezoelectric element and the acoustic lens; a material of an acoustic lens in a photoacoustic wave measurement apparatus or an ultrasound endoscope; and a material or the like of an acoustic lens in an ultrasound probe including capacitive micromachined ultrasonic transducers (cMUT) as an ultrasonic transducer array.

Specifically, the silicone resin for an acoustic wave probe of the present invention is preferably applied to, for example, an ultrasound diagnostic apparatus disclosed in JP2005-253751A and JP2003-169802A or an acoustic wave measurement apparatus such as a photoacoustic wave measurement apparatus disclosed in JP2013-202050A, JP2013-188465A, JP2013-180330A, JP2013-158435A, JP2013-154139A, or the like.

<<Acoustic Wave Probe>>

A configuration of an acoustic wave probe of the present invention will be described below in more detail based on a configuration of an ultrasound probe in an ultrasound diagnostic apparatus which is described in FIG. 1. The ultrasound probe is a probe which particularly uses an ultrasonic wave as an acoustic wave in an acoustic wave probe. For this reason, a basic configuration of the ultrasound probe can be applied to the acoustic wave probe as it is.

—Ultrasound Probe—

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end (the surface coming into contact with a living body which is a test object) as shown in FIG. 1. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

Inorganic piezoelectric bodies of so-called ceramics obtained by polarizing crystals, single crystals such as $LiNbO_3$, $LiTaO_3$, and $KNbO_3$, thin films of ZnO and AlN, $Pb(Zr,Ti)O_3$-based sintered body, and the like are widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent broadband characteristics, and excellent mass productivity and has less characteristic variations, is obtained is disclosed in JP2011-071842A or the like.

In the present invention, it is possible to preferably use any piezoelectric element material.

<Backing Material>

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

<Acoustic Matching Layer>

The acoustic matching layer 2 is provided in order to reduce the difference in acoustic impedance between the piezoelectric element layer 3 and a test object and to efficiently transmit and receive an ultrasonic wave.

A composition for an ultrasound probe of the present invention can preferably be used as a material for the acoustic matching layer since the difference in acoustic impedance ($1.4\times10^6$ to $1.7\times10^6$ kg/m$^2$/sec) between the piezoelectric element layer and a living body is small. The acoustic matching layer of the present invention preferably contains 10 mass % or more of a silicone resin for an acoustic wave probe obtained by subjecting the composition for an acoustic wave probe of the present invention to a vulcanization reaction.

<Acoustic Lens>

The acoustic lens 1 is provided in order to improve resolution by making an ultrasonic wave converge in a slice direction using refraction. In addition, it is necessary for the acoustic lens to achieve matching of an ultrasonic wave with acoustic impedance ($1.4\times10^6$ to $1.7\times10^6$ kg/m$^2$/sec in a case of a human body) of a living body which is a test object after being closely attached to the living body and to reduce ultrasonic attenuation of the acoustic lens 1 itself.

That is, sensitivity of transmission and reception of an ultrasonic wave is improved using a material of which the acoustic velocity is sufficiently lower than that of a human body, the ultrasound attenuation is low, and the acoustic impedance is close to a value of the skin of a human body, as the material of the acoustic lens 1.

The composition for an acoustic wave probe as a composition for an ultrasound probe of the present invention can also preferably be used as a material of the acoustic lens.

The operation of the ultrasound probe 10 having such a configuration will be described. The piezoelectric element layer 3 is resonated after applying voltage to the electrodes provided on both sides of a piezoelectric element, and an ultrasound signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

Particularly, a remarkable effect of improving the sensitivity can be checked from a transmission frequency of an ultrasonic wave of greater than or equal to about 5 MHz using the acoustic lens obtained from the composition for an ultrasound probe of the present invention as a general medical ultrasonic transducer. Particularly, a remarkable effect of improving the sensitivity can particularly be expected from a transmission frequency of an ultrasonic wave of greater than or equal to 10 MHz.

Hereinafter, an apparatus in which the acoustic lens obtained from the composition for an ultrasound probe of the present invention exhibits a function particularly regarding conventional problems will be described in detail.

The composition for an ultrasound probe of the present invention exhibits an excellent effect even with respect to other apparatuses disclosed below.

—Ultrasound Probe Including Capacitive Micromachined Ultrasonic Transducer (cMUT)—

In a case where cMUT apparatuses disclosed in JP2006-157320A, JP2011-71842A, and the like are used in an ultrasonic diagnostic transducer array, the sensitivity thereof generally becomes low compared to a transducer in which usual piezoelectric ceramics (PZT) is used.

However, it is possible to make up for deficient sensitivity of cMUT using the acoustic lens obtained from the composition for an acoustic wave probe of the present invention. Accordingly, it is possible to make the sensitivity of cMUT to performance of a conventional transducer.

The cMUT apparatus is manufactured through MEMS technology. Therefore, it is possible to provide an inexpensive ultrasound probe, of which mass productivity is higher than that of a piezoelectric ceramics probe, to the market.

—Photoacoustic Wave Measurement Apparatus Using Photo-Ultrasound Imaging—

Photoacoustic imaging (photo acoustic imaging: PAI) disclosed in JP2013-158435A or the like displays a signal strength of an ultrasonic wave or an image obtained by imaging the ultrasonic wave generated in a case where human tissue is adiabatically expanded using light (magnetic wave) with which the interior of a human body is irradiated.

Here, the amount of an acoustic pressure of an ultrasonic wave generated through light irradiation is minute, and therefore, there is a problem in that it is difficult to observe deeper regions of a human body.

However, it is possible to exhibit an effect effective for the problem using the acoustic lens obtained from the composition for an acoustic wave probe of the present invention.

—Ultrasound Endoscope—

In an ultrasonic wave in an ultrasound endoscope disclosed in JP2008-311700A or the like, a signal line cable is structurally long compared to that of a transducer for a body surface, and therefore, there is a problem of improving the sensitivity of the transducer accompanied by loss of the cable. Regarding this problem, it is said that there are no effective means for improving the sensitivity due to the following reasons.

First, in a case of an ultrasound diagnostic apparatus for a body surface, it is possible to install an amplifier circuit, an AD conversion IC, or the like at a distal end of the transducer. In contrast, the ultrasound endoscope is inserted into a body. Therefore, there is a small installation space within the transducer, and thus, it is difficult to install the amplifier circuit, the AD conversion IC, or the like at a distal end of the transducer.

Secondly, it is difficult to apply a piezoelectric single crystal employed in the transducer in the ultrasound diagnostic apparatus for a body surface onto a transducer with an ultrasonic transmission frequency of greater than or equal to 7 to 8 MHz due to physical properties and processing suitability. However, an ultrasonic wave for an endoscope is generally a probe having an ultrasonic transmission frequency of greater than or equal to 7 to 8 MHz, and therefore, it is also difficult to improve the sensitivity using piezoelectric single crystal material.

However, it is possible to improve the sensitivity of the ultrasonic transducer for an endoscope using the acoustic lens obtained from the composition for an acoustic wave probe of the present invention.

In addition, even in a case of using the same ultrasonic transmission frequency (for example, 10 MHz), the efficacy is particularly exhibited in a case of using the acoustic lens obtained from the composition for an acoustic wave probe of the present invention in the ultrasonic transducer for an endoscope.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like.

Example 1

54.0 parts by mass of a vinyl terminated diphenylsiloxane-dimethylsiloxane copolymer ("PDV-0535" manufactured by GELEST, INC. with a mass average molecular weight of 47,500 and a diphenylsiloxane amount of 5 mol %), 1.0 parts by mass of polymethylhydrosiloxane ("HMS-991" manufactured by GELEST, INC. with a mass average molecular weight of 1,600), and 45.0 parts by mass of truly spherical surface-treated silica ("QSG-30" manufactured by Shin-Etsu Chemical Co., Ltd. with an average primary particle diameter of 30 nm which was a surface-treated product with methyltrimethoxysilane and hexamethyldisilazane (HMDS) and had a methanol hydrophobicity degree of 67 mass %) were kneaded with a kneader for 2 hours at a set temperature of 23° C. to obtain a homogeneous paste. 0.05 parts by weight of a platinum catalyst solution (manufactured by GELEST, INC., trade name of "SIP6830.3" with 3 mass % of Pt concentration) was added to and mixed with the paste. Then, the mixture was subjected to defoamation under reduced pressure, placed in a metal mold of 150 mm×150 mm×2 mm depth, and subjected to heat treatment for 3 hours at 60° C. to produce a silicone resin for an acoustic wave probe (sheet of 150 mm long×150 mm wide×2 mm thick). Hereinafter, the silicone resin for an acoustic wave probe produced in this manner is referred to as a "silicone resin sheet".

Examples 2 to 14 and Comparative Examples 2 and 5

Predetermined silicone resin sheets were produced similarly to Example 1 except that the composition of the polysiloxane mixture of Example 1 was changed to the compositions disclosed in Table 1.

Examples 15 and 16 and Comparative Examples 3 and 4

Truly spherical surface-treated silica particles C1, C2, T1, and T2 having an average primary particle diameter and a methanol hydrophobicity described in Table 1 were obtained through similar processing except that the amounts of methanol, water, and 28% aqueous ammonia in a step (A1) in the example disclosed in Synthesis Example 1 of JP2007-99582A were changed.

A predetermined silicone resin sheet was produced in the same manner as in Example 1 except that the obtained truly spherical surface-treated silica particles were used as the silica particles (C).

Comparative Example 1

54.0 parts by mass of a vinyl terminated diphenylsiloxane-dimethylsiloxane copolymer ("PDV-0535" manufactured by GELEST, INC. with a mass average molecular weight of 47,500 and a diphenylsiloxane amount of 5 mol %), 1.0 parts by mass of polymethylhydrosiloxane ("HMS-991" manufactured by GELEST, INC. with a mass average molecular weight of 1,600), and 45.0 parts by mass of heteromorphic surface-treated fumed silica ("AEROSIL (registered trademark) R974 manufactured by NIPPON AEROSIL CO., LTD. with an average primary particle diameter of 12 nm which is a surface-treated product with dimethyldichlorosilane (DDS) and had a methanol hydrophobicity of 33 mass %) were kneaded with a kneader for 2 hours at a set temperature of 23° C. However, since the viscosity was too high, the kneader overloaded and stopped. Therefore, it was impossible to knead the mixture.

Comparative Example 6

54.0 parts by mass of a vinyl terminated diphenylsiloxane-dimethylsiloxane copolymer ("PDV-0535" manufactured by GELEST, INC. with a mass average molecular weight of 47,500 and a diphenylsiloxane amount of 5 mol %), 1.0 parts by mass of polymethylhydrosiloxane ("HMS-991" manufactured by GELEST, INC. with a mass average molecular weight of 1,600), and 45.0 parts by mass of heteromorphic non-treated fumed silica ("AEROSIL (registered trademark) 50 manufactured by NIPPON AEROSIL CO., LTD. with an average primary particle diameter of 30 nm without surface treatment which had a methanol hydrophobicity of 0 mass %) were kneaded with a kneader for 2 hours at a set temperature of 23° C. However, since the viscosity was too high, the kneader overloaded and stopped. Therefore, it was impossible to knead the mixture.

[Methanol Hydrophobicity]

50 ml of ion exchange water and 0.2 g of silica particles as samples were placed in a beaker at 25° C. and stirred with a magnetic stirrer, methanol was added dropwise thereto from a burette, and the amount (Xg) of methanol added dropwise until the whole sample settles was measured. The methanol hydrophobicity was calculated using the following equation.

$$\text{Methanol hydrophobicity(mass \%)} = X/(50+X) \times 100$$

[Viscosity Before Vulcanizing]

The viscosity of a paste before addition of a platinum catalyst was measured using "RheoStress RS6000" which is a trade name manufactured by HAAKE under the conditions of a temperature of 23° C. and a shear rate of 0.001 s$^{-1}$.

In Comparative Examples 1 and 6, it was impossible to obtain a homogeneous composition due to high viscosity, and therefore, it was impossible to measure the viscosity.

<Evaluation of Mechanical Strength and Ultrasonic Characteristics>

The following evaluation was performed on silicone resin sheets of Examples 1 to 16 and Comparative Examples 1 to 6.

[Hardness]

The type A durometer hardness of each of the obtained silicone resin sheets with a thickness of 2 mm was measured using a rubber hardness meter (trade name "RH-201A" manufactured by Excel co., Ltd.) in compliance with JIS K6253-3 (2012).

[Tear Strength Test]

A trouser-type test piece of a silicone resin sheet with a thickness of 2 mm was manufactured and the tear strength was measured in compliance with JIS K6252 (2007).

[Acoustic Impedance]

The density of each of the obtained silicone resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999). The acoustic velocity of an ultrasonic wave was measured at 25° C. using a sing-around type acoustic velocity measurement apparatus (a trade name of "UVM-2 type" manufactured by Ultrasonic Engineering Co., Ltd.) in compliance with JIS Z2353 (2003) and acoustic impedance was obtained from a sum of the density and the acoustic velocity which had been measured.

[Acoustic (Ultrasonic) Sensitivity]

A sinusoidal signal (a wave) of 5 MHz which had been output from an ultrasound oscillator (a function generator with a trade name of "FG-350" manufactured by IWATSU ELECTRIC CO., LTD.) was input into an ultrasound probe (manufactured by JAPAN PROBE), and an ultrasound pulse wave with a center frequency of 5 MHz was generated in water from the ultrasound probe. The magnitude of the amplitude before and after the generated ultrasonic wave passed through each of the obtained silicone resin sheet with a thickness of 2 mm was measured in a water temperature environment of 25° C. using an ultrasound receiver (an oscilloscope with a trade name of "VP-5204A" manufactured by Matsushita Electric Industrial Co., Ltd.) The acoustic (ultrasonic) attenuation of each material was compared with each other by comparing the acoustic (ultrasonic) sensitivities of each material.

The acoustic (ultrasonic) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained when the ultrasound oscillator receives an acoustic wave (ultrasonic wave) that the acoustic wave (ultrasonic wave) generated passes through a sheet and is reflected from an opposite side of the sheet.

$$\text{Acoustic(Ultrasonic)sensitivity} = 20 \times \text{Log}(Vs/Vin)$$

The obtained results were summarized and shown in Table 1.

In table 1, the mass average molecular weight of the polyorganosiloxane (A) and the polyorganosiloxane (B) is simply described as a molecular weight, and the type of each component is indicated by a trade name.

TABLE 1

|  |  |  | Example 1 | Example 2 | Example 3 | Example 4 | Example 5 | Example 6 | Example 7 | Example 8 |
|---|---|---|---|---|---|---|---|---|---|---|
| Mixed composition | Polyorganosiloxane (A) | Type | PDV-0535 | PDV-0541 | PDV-1641 | PDV-1635 | PDV-1631 | DMS-V52 | DMS-V46 | DMS-V42 |
|  |  | Molecular weight | 47,500 | 60,000 | 55,000 | 35,300 | 19,000 | 155,000 | 117,000 | 72,000 |
|  |  | Content [mass %] | 54.0 | 54.2 | 53.4 | 52.6 | 50.7 | 54.7 | 54.6 | 54.5 |
|  | Polyorganosiloxane (B) | Type | HMS-991 | HMS-991 | HPM-502 | HPM-502 | HPM-502 | HMS-991 | HMS-991 | HMS-991 |
|  |  | Molecular weight | 1,600 | 1,600 | 4,500 | 4,500 | 4,500 | 1,600 | 1,600 | 1,600 |
|  |  | Content [mass %] | 1.0 | 0.8 | 1.6 | 2.4 | 4.3 | 0.3 | 0.4 | 0.5 |
|  | Silica particles (C) | Type | QSG-30 | QSG-30 | QSG-30 | QSG-30 | QSG-30 | QSG-30 | QSG-30 | QSG-30 |
|  |  | Average primary particle diameter [nm] | 30 | 30 | 30 | 30 | 30 | 30 | 30 | 30 |
|  |  | Shape | True spherical shape | True spherical shape | True spherical shape | True spherical shape | True spherical shape | True spherical shape | True spherical shape | True spherical shape |
|  |  | Methanol hydrophobicity [mass %] | 67 | 67 | 67 | 67 | 67 | 67 | 67 | 67 |
|  |  | Content [mass %] | 45.0 | 45.0 | 45.0 | 45.0 | 45.0 | 45.0 | 45.0 | 45.0 |
| Evaluation | Viscosity [Pa · s] before vulcanizing |  | 120 | 150 | 150 | 140 | 120 | 190 | 180 | 160 |
|  | JIS hardness |  | 47 | 43 | 40 | 42 | 45 | 38 | 41 | 43 |
|  | Tear strength [N/cm] |  | 37 | 43 | 15 | 12 | 10 | >100 | >100 | 76 |
|  | Acoustic impedance [×10$^6$ kg/m$^2$/s] |  | 1.40 | 1.40 | 1.52 | 1.52 | 1.51 | 1.28 | 1.28 | 1.28 |
|  | Acoustic (ultrasonic) sensitivity [dB] |  | −69.0 | −69.2 | −69.6 | −69.8 | −69.9 | −69.0 | −69.2 | −69.2 |

TABLE 2

Continued from Table 1

|  |  |  | Example 9 | Example 10 | Example 11 | Example 12 | Example 13 | Example 14 | Example 15 | Example 16 |
|---|---|---|---|---|---|---|---|---|---|---|
| Mixed composition | Polyorganosiloxane (A) | Type | DMS-V41 | DMS-V31 | PDV-0535 | PDV-0535 | PDV-0535 | PDV-0535 | PDV-0535 | PDV-0535 |
|  |  | Molecular weight | 62,700 | 28,000 | 47,500 | 47,500 | 47,500 | 47,500 | 47,500 | 47,500 |
|  |  | Content [mass %] | 54.4 | 53.5 | 54.0 | 54.0 | 54.0 | 54.0 | 54.0 | 54.0 |
|  | Polyorganosiloxane (B) | Type | HMS-991 | HMS-991 | HMS-991 | HMS-991 | HMS-991 | HMS-991 | HMS-991 | HMS-991 |
|  |  | Molecular weight | 1,600 | 1,600 | 1,600 | 1,600 | 1,600 | 1,600 | 1,600 | 1,600 |
|  |  | Content [mass %] | 0.6 | 1.5 | 1.0 | 1.0 | 1.0 | 1.0 | 1.0 | 1.0 |
|  | Silica particles (C) | Type | QSG-30 | QSG-30 | QSG-80 | YA050C-SP3 | MSP-011 | NAX50 | C1 | C2 |
|  |  | Average primary particle diameter [nm] | 30 | 30 | 80 | 50 | 30 | 30 | 18 | 97 |
|  |  | Shape | True spherical shape | True spherical shape | True spherical shape | True spherical shape | Heteromorphic shape | Heteromorphic shape | True spherical shape | True spherical shape |
|  |  | Methanol hydrophobicity [mass %] | 67 | 67 | 67 | 47 | 41 | 28 | 61 | 76 |
|  |  | Content [mass %] | 45.0 | 45.0 | 45.0 | 45.0 | 45.0 | 45.0 | 45.0 | 45.0 |
| Evaluation | Viscosity [Pa · s] before vulcanizing |  | 150 | 130 | 40 | 2,500 | 4,600 | 8,600 | 280 | 30 |
|  | JIS hardness |  | 45 | 51 | 45 | 50 | 51 | 53 | 49 | 44 |
|  | Tear strength [N/cm] |  | 48 | 13 | 11 | 20 | 26 | 8 | 52 | 10 |
|  | Acoustic impedance [×10$^6$ kg/m$^2$/s] |  | 1.28 | 1.27 | 1.40 | 1.40 | 1.41 | 1.40 | 1.40 | 1.40 |
|  | Acoustic (ultrasonic) sensitivity [dB] |  | −69.3 | −69.6 | −68.9 | −68.8 | −69.7 | −69.9 | −69.7 | −69.6 |

TABLE 3

Continued from Table 1

|  |  |  | Comparative Example 1 | Comparative Example 2 | Comparative Example 3 | Comparative Example 4 | Comparative Example 5 | Comparative Example 6 |
|---|---|---|---|---|---|---|---|---|
| Mixed composition | Polyorganosiloxane (A) | Type | PDV-0535 | PDV-0535 | PDV-0535 | PDV-0535 | PDV-0535 | PDV-0535 |
|  |  | Molecular weight | 47,500 | 47,500 | 47,500 | 47,500 | 47,500 | 47,500 |
|  |  | Content [mass %] | 54.0 | 78.5 | 54.0 | 54.0 | 54.0 | 54.0 |
|  | Polyorganosiloxane (B) | Type | HMS-991 | HMS-991 | HMS-991 | HMS-991 | HMS-991 | HMS-991 |
|  |  | Molecular weight | 1,600 | 1,600 | 1,600 | 1,600 | 1,600 | 1,600 |
|  |  | Content [mass %] | 1.0 | 1.5 | 1.0 | 1.0 | 1.0 | 1.0 |
|  | Silica particles (C) | Type | R974 | R974 | T1 | T2 | QSG-100 | 50 |
|  |  | Average primary particle diameter [nm] | 12 | 12 | 16 | 104 | 110 | 30 |
|  |  | Shape | Heteromorphic shape | Heteromorphic shape | True spherical shape | True spherical shape | True spherical shape | Heteromorphic shape |
|  |  | Methanol hydrophobicity [mass %] | 33 | 33 | 59 | 70 | 67 | 0 |
|  |  | Content [mass %] | 45.0 | 20.0 | 45.0 | 45.0 | 45.0 | 45.0 |
| Evaluation | Viscosity [Pa · s] before vulcanizing |  | Kneading cannot be performed since viscosity is too high | 16,000,000 | 320 | 25 | 20 | Kneading cannot be performed since viscosity is too high |
|  | JIS hardness |  |  | 51 | 51 | 43 | 42 |  |
|  | Tear strength [N/cm] |  |  | 22 | 73 | 6 | 4 |  |
|  | Acoustic impedance [×10$^6$ kg/m$^2$/s] |  |  | 1.19 | 1.40 | 1.40 | 1.39 |  |
|  | Acoustic (ultrasonic) sensitivity [dB] |  |  | −71.2 | −70.3 | −70.1 | −70.9 |  |

<Notes of Table>
[Polyorganosiloxane Component (A)]
  PDV-0535: trade name, vinyl terminated diphenylsiloxane-dimethylsiloxane copolymer manufactured by GELEST, INC., mass average molecular weight of 47,500, diphenylsiloxane amount of 5 mol %
  PDV-0541: trade name, vinyl terminated diphenylsiloxane-dimethylsiloxane copolymer manufactured by GELEST, INC., mass average molecular weight of 60,000, diphenylsiloxane amount of 5 mol %
  PDV-1641: trade name, vinyl terminated diphenylsiloxane-dimethylsiloxane copolymer manufactured by GELEST, INC., mass average molecular weight of 55,000, diphenylsiloxane amount of 16 mol %
  PDV-1635: trade name, vinyl terminated diphenylsiloxane-dimethylsiloxane copolymer manufactured by GELEST, INC., mass average molecular weight of 35,300, diphenylsiloxane amount of 16 mol %
  PDV-1631: trade name, vinyl terminated diphenylsiloxane-dimethylsiloxane copolymer manufactured by GELEST, INC., mass average molecular weight of 19,000, diphenylsiloxane amount of 16 mol %
  DMS-V52: trade name, vinyl terminated polydimethylsiloxane manufactured by GELEST, INC., mass average molecular weight of 155,000
  DMS-V46: trade name, vinyl terminated polydimethylsiloxane manufactured by GELEST, INC., mass average molecular weight of 117,000
  DMS-V42: trade name, vinyl terminated polydimethylsiloxane manufactured by GELEST, INC., mass average molecular weight of 72,000
  DMS-V41: trade name, vinyl terminated polydimethylsiloxane manufactured by GELEST, INC., mass average molecular weight of 62,700
  DMS-V31: trade name, vinyl terminated polydimethylsiloxane manufactured by GELEST, INC., mass average molecular weight of 28,000
[Polyorganosiloxane Component (B)]
  HMS-991: trade name, methylhydrosiloxane polymer manufactured by GELEST, INC., mass average molecular weight of 1,600
  HPM-502: trade name, methylhydrosiloxane-phenylmethylsiloxane copolymer manufactured by GELEST, INC., mass average molecular weight of 4,500
[Surface-Treated Silica Particles (C)]
  True spherical shape: having Wardell's sphericity of 0.9 to 1
  Heteromorphic shape: having Wardell's sphericity of less than 0.9
  QSG-30: trade name manufactured by Shin-Etsu Chemical Co., Ltd., average primary particle diameter of 30 nm, surface-treated product with methyltrimethoxysilane (hereinafter, abbreviated as MTMS) and hexamethyldisilazane (hereinafter, abbreviated as HMDS), true spherical shape, methanol hydrophobicity of 67%
  QSG-80: trade name manufactured by Shin-Etsu Chemical Co., Ltd., average primary particle diameter of 80 nm, surface-treated product with MTMS and HMDS, true spherical shape, methanol hydrophobicity of 67%
  YA050C-SP3: manufactured by Admatechs, average primary particle diameter of 50 nm, surface-treated product with phenyltrimethoxysilane, true spherical shape, methanol hydrophobicity of 47%
  MSP-011: manufactured by TAYCA, average primary particle diameter of 30 nm, surface-treated product with MTMS and HMDS, heteromorphic shape, methanol hydrophobicity of 41%
  AEROSIL NAX50: trade name manufactured by NIPPON AEROSIL CO., LTD., average primary particle diameter of 30 nm, fumed silica, surface-treated product with HMDS, heteromorphic shape, methanol hydrophobicity of 28%
  AEROSIL R974: manufactured by NIPPON AEROSIL CO., LTD., average primary particle diameter of 12 nm, surface-treated product with dimethyldichlorosilane, heteromorphic shape, methanol hydrophobicity of 33%
  QSG-100: trade name manufactured by Shin-Etsu Chemical Co., Ltd., average primary particle diameter of 110 nm, surface-treated product with MTMS and HMDS, methanol hydrophobicity of 67%
  AEROSIL 50: trade name, manufactured by NIPPON AEROSIL CO., LTD., average primary particle diameter of 30 nm, no surface treatment, heteromorphic shape, methanol hydrophobicity of 0%

C1, C2, T1, T2: Silica particles synthesized above

">100 (Examples 6 and 7)" means that the tear strength is greater than 100 N/cm.

As is apparent from Table 1, in Examples 1 to 16, the viscosity of each composition for an acoustic wave probe in a state before vulcanizing was low, and all of the silicone resins for an acoustic wave probe could obtain high resin hardness and tear strength and excellent acoustic impedance while maintaining the acoustic (ultrasonic) sensitivities greater than or equal to −70 dB.

In contrast, the viscosity of the composition for an acoustic wave probe before vulcanizing was high in Comparative Example 1 in which silica particles having an average primary particle diameter of 12 nm are used, and therefore, it was impossible to knead the composition. In addition, in Comparative Example 2 in which the content of silica particles was reduced, even though it was possible to knead the composition, it was impossible to disperse the silica particles, the silicone resin for an acoustic wave probe had poor acoustic sensitivity, and the acoustic impedance was not close to a human body. In Comparative Example 3 in which silica particles having an average primary particle diameter of 16 nm are used, the acoustic sensitivity is not sufficient. In Comparative Examples 4 and 5 in which silica particles having an average primary particle diameter exceeding 100 nm were used, the tear strength was low and the acoustic sensitivity was poor. In Comparative Example 6 in which silica particles of which the average primary particle diameter was within the range of the present invention and which were not subjected to surface treatment were used, the viscosity of the composition for an acoustic wave probe before vulcanizing was high, and therefore, it was impossible to knead the composition.

From the results, it can be seen that the composition for an acoustic wave probe of the present invention is useful for a medical member. In addition, it can be seen that the silicone resin for an acoustic wave probe of the present invention can also be suitably used in the acoustic lens and/or the acoustic matching layer of the acoustic wave probe, the acoustic wave measurement apparatus, and the ultrasound diagnostic apparatus. Particularly, the composition for an acoustic wave probe and the silicone resin for an acoustic wave probe can be suitably used in the ultrasound probe in which cMUT is used as an ultrasonic diagnostic transducer array, the photoacoustic wave measurement apparatus, and the ultrasound endoscope for the purpose of improving the sensitivity.

The present invention has been described using an embodiment thereof. However, it is considered that, unless otherwise specified, even the detailed description of the invention is not limited and is necessarily widely interpreted without departing from the gist and the range of the invention shown in the attached Claims.

Priority is claimed on JP2016-014141, filed Jan. 28, 2016, and the entire content of which is incorporated herein by reference as a part of the description of the present specification.

EXPLANATION OF REFERENCES

1: acoustic lens
2: acoustic matching layer
3: piezoelectric element layer
4: backing material
7: housing
9: cord
10: ultrasound probe

What is claimed is:

1. A composition for an acoustic wave probe, comprising:
a polysiloxane mixture containing polysiloxane having a vinyl group, polysiloxane having two or more Si—H groups in a molecular chain, and silica particles of which an average primary particle diameter exceeds 16 nm and less than 100 nm and which are subjected to surface treatment,
wherein 25 to 70 parts by mass of the silica particles subjected to surface treatment are contained in 100 parts by mass in total of the polysiloxane mixture, and
wherein a methanol hydrophobicity of the silica particles subjected to surface treatment is 40 to 80 mass %.

2. The composition for an acoustic wave probe according to claim 1,
wherein 29.9 to 74.9 parts by mass of the polysiloxane having a vinyl group and 0.1 to 20 parts by mass of the polysiloxane having two or more Si—H groups in a molecular chain are contained in 100 parts by mass in total of the polysiloxane mixture.

3. The composition for an acoustic wave probe according to claim 1,
wherein the silica particles subjected to surface treatment are silica particles subjected to surface treatment using a silane compound.

4. The composition for an acoustic wave probe according to claim 3,
wherein the silica particles subjected to surface treatment are silica particles subjected to surface treatment using a trimethylsilylating agent.

5. The composition for an acoustic wave probe according to claim 1,
wherein the silica particles subjected to surface treatment are truly spherical.

6. The composition for an acoustic wave probe according to claim 1,
wherein the polysiloxane having a vinyl group has a phenyl group.

7. The composition for an acoustic wave probe according to claim 1,
wherein a mass average molecular weight of the polysiloxane having a vinyl group is 20,000 to 200,000.

8. The composition for an acoustic wave probe according to claim 1,
wherein a mass average molecular weight of the polysiloxane having a vinyl group is 40,000 to 150,000.

9. The composition for an acoustic wave probe according to claim 1,
wherein the polysiloxane having two or more Si—H groups in a molecular chain has a phenyl group.

10. The composition for an acoustic wave probe according to claim 1, further comprising:
0.00001 to 0.01 parts by mass of platinum or a platinum compound with respect to 100 parts by mass of the polysiloxane mixture.

11. A silicone resin for an acoustic wave probe which is obtained by vulcanizing the composition for an acoustic wave probe according to claim 1.

12. An acoustic wave probe comprising:
at least one selected from the group consisting of: an acoustic lens made of the silicone resin for an acoustic wave probe according to claim 11, and an acoustic matching layer made of the silicone resin for an acoustic wave probe according to claim 11.

13. An acoustic wave measurement apparatus comprising:
the acoustic wave probe according to claim 12.

14. An ultrasound diagnostic apparatus comprising:
the acoustic wave probe according to claim 12.

15. An ultrasound probe comprising:
a capacitive micromachined ultrasonic transducer as an ultrasonic transducer array; and
an acoustic lens containing the silicone resin for an acoustic wave probe according to claim 11.

16. A photoacoustic wave measurement apparatus comprising:
an acoustic lens containing the silicone resin for an acoustic wave probe according to claim 11.

17. An ultrasound endoscope comprising:
an acoustic lens containing the silicone resin for an acoustic wave probe according to claim 11.

* * * * *